(12) United States Patent
Semmelhack et al.

(10) Patent No.: US 7,652,172 B2
(45) Date of Patent: Jan. 26, 2010

(54) EXPEDITIOUS SYNTHESIS OF DPD

(75) Inventors: Martin F. Semmelhack, Princeton, NJ (US); Shawn R. Campagna, Hamilton, NJ (US); Bonnie L. Bassler, Princeton, NJ (US); Michael J. Federle, Pennington, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 11/575,557

(22) PCT Filed: Sep. 20, 2005

(86) PCT No.: PCT/US2005/033648

§ 371 (c)(1),
(2), (4) Date: Sep. 30, 2008

(87) PCT Pub. No.: WO2006/034269

PCT Pub. Date: Mar. 30, 2006

(65) Prior Publication Data

US 2009/0018368 A1    Jan. 15, 2009

Related U.S. Application Data

(60) Provisional application No. 60/611,551, filed on Sep. 20, 2004.

(51) Int. Cl.
*C07C 45/00* (2006.01)
*C07D 307/00* (2006.01)

(52) U.S. Cl. .................. 568/386; 568/388; 568/413; 549/430; 549/476

(58) Field of Classification Search .................. 568/388, 568/413; 549/430, 476
See application file for complete search history.

(56) References Cited

OTHER PUBLICATIONS

Semmelhack et al., 2005, Org. Let. 7:569.
Zhu et al., Catalytic Mechanism of S-Ribosylhomocysteinase (LUXS): Stereochemical Course and Kinetic Isotope Effect of Proton Transfer Reactions. Biochemistry. 2004, vol. 43, pp. 10166-10172.
Semmelhack et al., Boron Binding with the Quorum Sensing Signal AL-2 and Analogues. Organic Letters. 2004, vol. 6, No. 15, pp. 2635-2637.
Wu et al., Synthesis and Biological Evaluation of 1 alpha-hydroxy-25 (R and S)-25, 26-Epoxy-23yne Vitamin D3 and 1 alpha, 25(R and S), 26-Trihydroxy-23-yne Vitamin D3. Bioorganic & Medicinal Chemistry Letters. 1997, vol. 7, No. 7, pp. 929-932.

Aube, J. et al., (2S, 3S, 5S)- and (2S, 3S, 5R)-5-Carboxaldehyde-2,3-diphenyl-1,4-dioxane as Surrogates for Optically Pure 2,3-O-lsopropylideneglyceraldehyde in Asymmetric Synthesis, (1992) Tetrahedron Vo. 48, No. 45, pp. 9819-9826.
Chen, X. et al., Structural identification of a bacterial quorum-sensing signal containing boron, (2002) Nature vol. 415, pp. 545-549.
Cornell, K.A. et al., Cloning and expression of *Escherichia coli* 5'-methylthioadenosine/S-adenosylhomocysteine nucleosidase: Identification of the pfs gene product, (1998) Biochim. Biophys. Acta 1396, pp. 8-14.
Dickson, A.G., Thermodynamics of the dissociation of boric acid in synthetic seawater from 273.15 to 318.15K, (1990) Deep-Sea Research, vol. 37, pp. 755-766.
Federle, M. et al., Interspecies communication in bacteria, (2003) J. Clin. Invest., vol. 112, No. 9, pp. 1291-1299.
Grauert, M. et al., Reactions of Metallated Bislactim Ethers of cyclo(-L-Val-Gly-) with (R)- and (S)-Glyceraldehyde and with (S)-Lactaldehyde, (1985) Liebigs, Ann. Chem., pp. 1817-1824.
Lewis, H. A. et al., A Structural Genomics Approach to the Study of Quorum Sensing: Crystal Structures of Three LuxS Orthologs, (2001), Structure, vol. 9, pp. 527-537.
Lorand, J.P. et al., Polyol Complexes and Structure of the Benzeneboronate Ion, (1959) J. Org. Chem., vol. 24, pp. 769-774.
Meijler, M.M. et al., Synthesis and Biological Validation of a Ubiquitous Quorum-Sensing Molecule, (2004), Angew. Chem. Int Ed. Engl. 43, pp. 2106-2108.
Michel, P. et al., Synthesis of Enantiomers of Butane-1,2-diacetal-Protected Glyceraldehyde and of (R,R)-Butane-1,2-diacetal-Protected Glycolic Acid, (2003), Synthesis No. 10, pp. 1598-1602.
Miller, S. T. et al., *Salmonella typhimurium* Recognizes a Chemically Distinct Form of the Bacterial Quorum-Sensing Signal A1-2, (2004), Mol. Cell., vol. 15, pp. 677-687.
Schauder, S. et al., The LuxS family of bacterial autoinducers: biosynthesis of a novel quorum-sensing signal molecule, (2001) Mol. Bicrobiol. vol. 41, pp. 463-476.
Schmid, C.R. et al., 2,3-0-(e-Pentylidene)-D-glyceraldehyde and 2,3-0-(3-Pentylidene)-L-glyceraldehyde: Convenient Glyceraldehyde Surrogates Obtained via a Novel Periodate-Based Oxdation System, (1992) Synthesis, pp. 587-590.
Slaughter, J.C. , The naturally occurring furanones: formation and function from pheromone to food, (1999) Biol. Rev. vol. 74, pp. 259-276.

(Continued)

*Primary Examiner*—Sikarl A Witherspoon
(74) *Attorney, Agent, or Firm*—Volpe and Koenig, P.C.

(57) ABSTRACT

This invention provides a practical synthesis route for 4,5-dihydroxypentane-2,3-dione (DPD), an unstable small molecule which is proposed to be the source of universal signaling agents for quorum sensing in bacteria. The synthesis route includes new intermediates and allows preparation of isotopically-labeled DPD and ent-DPD. The method provides sufficient quantities of DPD for study of spontaneous binding of borate to DPD, the signal for the marine bacteria *V. harveyi.*

8 Claims, 5 Drawing Sheets

OTHER PUBLICATIONS

Springsteen, G. et al., A detailed examination of boronic acid-diol complexation, (2002), Tetrahedron 58, pp. 5291-5300.

Surette, M.G. et al., Quorum sensing in *Escherichia coli, Salmonella typhimurium*, and *Vibrio harveyi*: A new family of genes responsible for autoinducer production, (1999), Proc. Natl. Acad. Sci. USA vol. 96, pp. 1639-1644.

Danishefsky, S. et al., On The Acetoxylation of 2,3-Dihydro-4-Pyrones: A concise, Fully Synthetic Route To The Glucal Stereochemical Series, (1985) Tehtrahedron Letters 41, pp. 3411-3412.

Vekemans et al., Vitamin-C- and isovitamin-C-derived chemistry., (1985) Recl. Tray. Chim. Pays-Bas. 104, pp. 266-272.

Winzer, K. et al., LuxS: its role in central metabolism and the in vitro synthesis of 4-hydroxy-5-methyl-3(2H)-furanone, (2002) Microbiology 148, pp. 909-922.

Xavier, K.B. et al., LuxS quorum sensing: more than just a numbers game (2003) Curr. Opin. Microbiol. 6, 191-197.

Yoshida, J. et al., Total Synthesis of Symbioramide a Novel Ca2+-ATPase Activator from Symbiodinium sp., (1992) J. Chem. Soc. Perkin Trans. 1, pp. 343-350.

Zibuck, R. et al., Note on the Preparation of 1,2-Diketones from Acetylenes, (1988) Helvetica Chimica Acta vol. 71, pp. 237-240.

Zhu, et al., Catalytic Mechanism of S-Ribosylhomocysteinase (LuxS): Direct Observation of Ketone Intermediates by 13C NMR Spectroscopy, (2003) J. Am. Chem. Soc. 125, pp. 13379-13381.

EXPEDITIOUS SYNTHESIS OF DPD

This application claims benefit under 35 U.S.C. §119(e) of U.S. Provisional Ser. No. 60/611,551, filed Sep. 20, 2004, which is incorporated herein by reference in its entirety.

GOVERNMENT INTERESTS

This invention was funded in part through grants from the National Institutes of Health. Therefore, the federal government has certain rights in this invention.

FIELD OF THE INVENTION

This invention provides a practical synthesis route for 4,5-dihydroxypentane-2,3-dione (DPD), a relatively unstable small molecule which is proposed to be the source of universal signaling agents for quorum sensing in bacteria. The synthesis route includes new intermediates and allows preparation of isotopically-labeled DPD and ent-DPD. The method provides sufficient quantities of DPD for study of spontaneous binding of borate to DPD, the signal for the marine bacteria $V.$ $harveyi$.

BACKGROUND OF THE INVENTION

DPD (1) is an enigmatic molecule. It has been known since 1971 as the product of catabolism of S-adenosylhomocysteine in many bacteria (Duerre et al. 1971); and, more recently, it is proposed to be the core molecule from which all bacterial AI-2 signaling molecules are derived (Miller et al. 2004). These molecules are widely used in inter-species communication in the bacterial world (Federle et al. 2001). It is a simple molecule, but was reported to be quite unstable toward rearrangement (Winzer et al. 2002; Slaughter et al. 1999) and oligomerization (Semmelhack et al. 2004; Meijler et al. 2004), and has only recently been synthesized and tentatively characterized in dilute solution (Meijler et al. 2004).

Figure 1A:
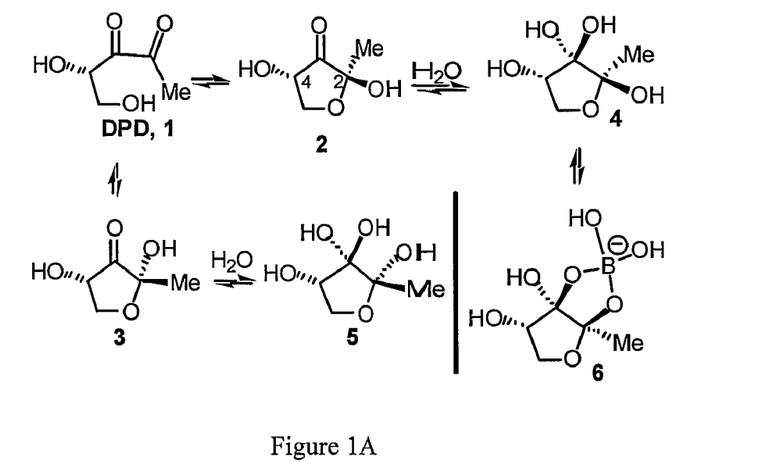
FIG. 1A illustrates the biological forms of DPD (1-6).

FIG. 1A shows that DPD can exist as an equilibrium mixture of three isomers (1,2, and 3), hydrated versions (4 and 5), and borate complexes (e.g., 6), collectively known as autoinducer 2 (AI-2) (Miller et al. 2004). $V.$ $harveyi$ recognizes the 2,3-borate diester (6) of the hydrated α-anomer (4) of DPD as AI-2 (Chen et al. 2002). $S.$ $typhimurium$ recognizes the hydrated β-anomer (5) of DPD without borate (Miller et al. 2004). The incorporation of borate into the AI-2 signal may be a function of the natural habitat of the bacteria. $V.$ $harvyei$ is a marine bacterium that lives in an environment with highborate concentration compared to $S.$ $typhimurium$, an enteric bacterium.

An efficient synthesis strategy for DPD allows characterization of DPD isomers, hydration processes, and boron complexation. The availability of much larger quantities of DPD than previously obtainable (either enzymatically or by a less efficient synthetic route should facilitate understanding DPD's role in bacterial quorum sensing for many species.

SUMMARY OF THE INVENTION

The present invention relates to an efficient and practical synthesis for DPD, its isomers and isotopically-labeled DPD. The availability of large quantities of DPD, as well as isotopically-labeled versions thereof, allows a detailed study of the isomerization, hydration, and boron complexation phenomena of DPD and aids in elucidation of DPD's role in bacterial quorum sensing.

One aspect of the invention relates to a method to synthesize protected DPD. Protected DPD can be purified and isolated as a solid, permitting storage of large quantities of this DPD precursor.

It has been discovered in accordance with this invention that DPD is stable under acidic conditions and that conversion of protected DPD to DPD proceeds efficiently and to near completion (as much as 95-99% removal of the protection group. Hence, another aspect of the invention takes advantage of this characteristic. Protected DPD is prepared in acid solutions and after hydroylsis of the protecting group, the pH is adjusted, and the solution used (directly or with dilution) in biological and other evaluations. For biological evaluations, the by-product of deprotection does not interfere with biological quorum sensing assays, at least when the protecting group is cyclohexylidene.

Figure 1B:
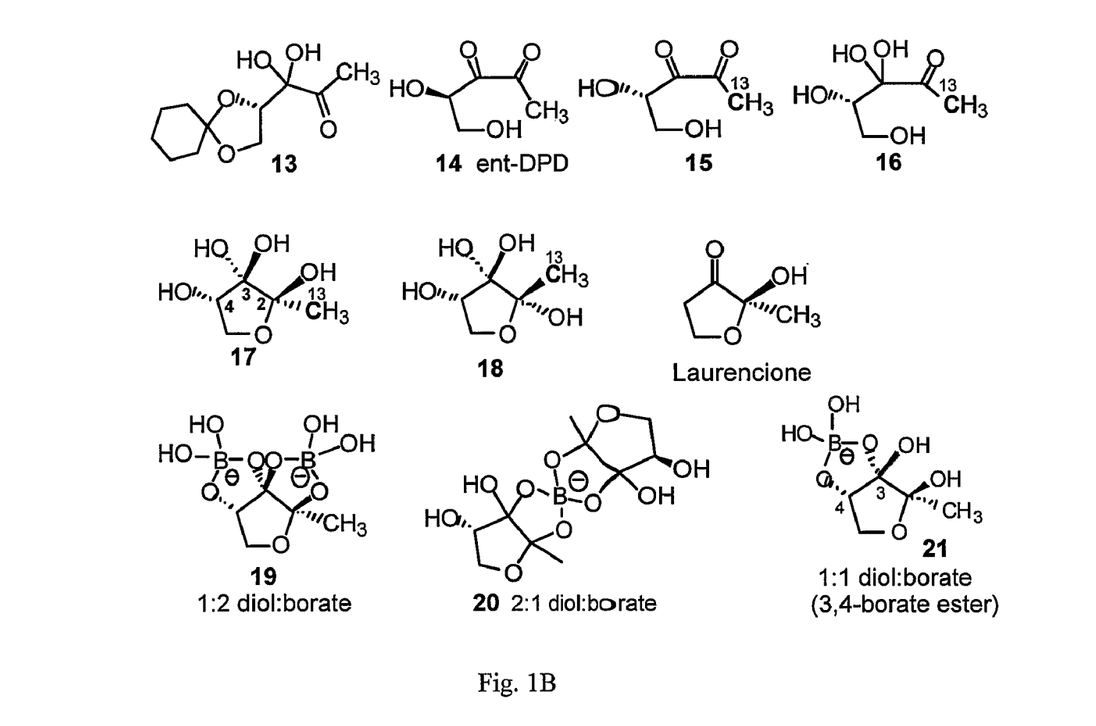
FIG. 1B illustrates various DPD derivatives (13-21).

Yet another aspect of the invention relates to the novel chemical intermediates used in synthesis of DPD as well as the isotopically-labeled forms of DPD and ent-DPD, and the pharmaceutically acceptable salts, if relevant. These intermediates include compounds 10, 11 and 12 of the invention (FIG. 2A) and the isotopically-labeled intermediates include compounds 15-18 as well as their $^{14}C$ labeled counterparts (FIG. 1B).

DETAILED DESCRIPTION OF THE INVENTION

Synthetic Methods

For the synthesis of the protected DPD molecules, the method involves (a) reacting gluconic acid γ-lactone with dimethoxycyclohexanone for a time and under conditions to produce 5,6-O-cyclohexylideneglucono-1,4-lactone; (b) subjecting the lactone to oxidative cleavage to produce 2,3-O-cyclohexylideneglyceraldehyde; (c) halogenating the glyceraldehyde molecule under conditions to produce 1,1-dihalo-3,4-cyclohexylidenedioxy but-1-ene ("dihaloalkene"); (d) purifying the dihaloalkene before reacting converting its alkene moiety to an alkyne anion; (e) quenching the anion by one of two routes, by reacting the alkyne anion with i) a methylating agent to produce 1,1-dihalo-3,4-cyclohexylidenedioxypent-3-yne, or ii) with water to produce 1,1-dibromrn-3,4-cyclohexylidenedioxybut-3-yne and subsequently methylating that compound to produce 1,1-dibromo-3,4-cyclohexylidenedioxypent-3-yne, and recovering that alkyne; (f) oxidizing that alkyne in non-aqueous solution under conditions to thereby produce 4,5-cyclohexylidene-dioxy-2,3-pentadione, which is the protected DPD molecule; and (g) recovering protected DPD.

When the gluconic acid γ-lactone starting material is a racemic mixture of the L- and D-stereoisomers of gluconic acid γ-lactone, then the protected DPD is a racemic mixture of (S)-4,5-cyclohexylidenedioxy-2,3-pentadione and (R)-4,5-cyclohexylidenedioxy-2,3-pentadione (racemic DPD). The present method also allows stereospecific synthesis of DPD and ent-DPD. When the gluconic acid γ-lactone starting material is L-gluconic acid γ-lactone, the protected DPD is (S)-4,5-cyclohexylidenedioxy-2,3-pentadione (DPD, 1). When the gluconic acid γ-lactone starting material is D-gluconic acid γ-lactone, the protected DPD is (R)-4,5-cyclohexylidenedioxy-2,3-pentadione (ent-DPD, 14).

For step (a), the reaction of gluconic acid γ-lactone with dimethoxycyclohexanone to produce 5,6-O-cyclohexylideneglucono-1,4-lactone is preferably done according to the method of Vekemans et al. 1985. Other methods known to those of skill in the art can be used and those giving a high yield of the lactone are preferred.

The lactone can be used directly without further purification in step (b) or can be purified before being subjected to oxidative cleavage to produce 2,3-O-cyclohexylideneglyceraldehyde. The oxidative cleavage preferably uses $KIO_4$ as described in Example 3. These conditions can be varied as known by those of skill in the art. Moreover, other oxidation methods that lead to the glyceraldehyde can be used.

For step (c), the glyceraldehyde is halogenated to produce 1,1-dihalo-3,4-cyclohexylidenedioxybut-1-ene. Halogenation can be accomplished using fluorine, chlorine, bromine or iodine and halogenation methods are well known in the art. The preferred halogenation method is bromination according to the method of Yoshida et al. 1992), see Example 4, or other variation of the Corey-Fuchs protocol. If necessary, the dihaloalkene is purified before further use, and this is preferable for the dibromoalkene.

In step (d), the alkene moiety of the dihaloalkene is converted to an alkyne anion with concomitant loss of the halogens. The alkyne anion can be quenched in step (e) to produce the alkyne by either of two routes and it is this point in the synthesis that allows introduction of carbon isotopes $^{13}C$ or $^{14}C$.

By one route, the alkyne anion is methylated to produce 1,1-dihalo-3,4-cyclohexylidenedioxypent-3-yne. Methylation reagents and conditions are well known and isotopically substituted methylation agents, such as $^{13}CH_3I$ and $^{14}CH_3I$ are readily obtainable. The alkyne should be purified before further use in the synthesis, but this may be optional under some conditions.

By the other route, the anion is quenched with water to produce 1,1-dibromo-3,4-cyclohexylidenedioxybut-3-yne and that molecule is subsequently methylated to produce 1,1-dibromo-3,4-cyclohexylidenedioxypent-3-yne. The methylation step of this route can be done as described in the paragraph above, see also, e.g., Example 5. Quenching with water before methylation appears to improve the yield of the alkyne. This route is also useful for isotopically labeling the compounds, see, e.g., Example 7. The alkyne should be purified before further use in the overall synthesis, but this may be optional under some conditions.

The next step, (f), involves oxidizing the alkyne in non-aqueous solution to produces 4,5-cyclohexylidenedioxy-2,3-pentadione (i.e., the protected DPD molecule). The preferred oxidation protocol uses $RuO_{2}, NaIO_4$ and produces the protected DPD is high yield that can be readily purified. This method is that of Seebach (Zibuch et al. 1988) but other oxidation methods are suitable. The method of Seebach provides excellent yields.

The Examples provide details of these syntheses steps and those of skill in the art know how to vary solvents, temperature and reactions conditions to achieve these synthetic steps. Methods of purifying the various intermediates and compounds described herein are also well known to those of skill in the art. The examples illustrate, but should not be considered limiting to, a variety of purification schemes.

In a variation on the above method, the synthesis can begin by preparing an 5,6-O-alkylidene-protected gluconic acid γ-lactone having a protecting group represented by the formula wherein R is independently alkyl having from 1 to 8 carbon atoms, aryl, or when taken together, form a cycloalkyl ring having from 3 to 8 carbon atoms. The remainder of the overall synthesis then proceeds as described in accordance with the invention.

As used herein, "alkyl" means both branched- and straight-chain, saturated aliphatic hydrocarbon groups having 1 to 8 carbon atoms. Alkyl groups include, but are not limited to, for example, methyl, ethyl, propyl, isopropyl, butyl, isobutyl, and the like. The cycloalkyl ring has from 3 to 8 carbon atoms, and include cyclobutyl, cyclopentyl, cyclohexyl and the like.

As used herein, "aryl" includes "aryl" and "substituted aryl." Thus "aryl" of this invention means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. The presence of substitution on the aryl group is optional, but when present, the substituents can be halo, alkyl, alkoxy, hydroxyl, amino, cyano, nitro, trifluoromethyl, acylamino or carbamoyl, provided that such substituents do not interfere with the synthesis, e.g., by necessitating use of conditions that are not compatible with a step in the synthesis.

As used herein, "stable compound" or "stable structure" means a compound that is sufficiently robust to survive isolation to a useful degree of purity from a reaction mixture. As those of skill in the art appreciate, the actual chemical stability of each compound will, however, vary depending on the particular substituents and their positions relative to one another. Methods to measure chemical stability are known to those of skill in the art.

Another aspect of the invention provides a method of converting protected DPD to DPD and is applicable for use with any protected DPD molecule, i.e., whether it is a protected DPD made according to the above synthetic pathway or a different pathway and whether it has a different protecting group (including but not limited to alkylidene protection groups described herein or other 1,2-diol protecting groups). To remove the protecting group, an amount of protected DPD in an aqueous solution under acidic conditions is allowed to hydrolyze. Hydrolysis goes to near completion under these conditions (>95% to >99% complete depending on the duration, temperature and pH. Hydrolysis of at least about 95% or more is considered near completion. The hydrolysis thus produces a stable solution of DPD under the appropriate acidic conditions. The protected DPD can be suspended in an aqueous solution having an acidic pH to allow the reaction to proceed or the protected DPD can be suspended in an aqueous solution which is subsequently acidified to the desired pH. The pH for hydrolysis is preferably less than about 3, preferably from about 0.5 to 2.0 and more preferably from about 1.3 to about 1.5.

As with the synthetic pathway, the protected DPD can be a racemic mixture or a stereoisomer, i.e., (S)-4,5-cyclohexylidenedioxy-2,3-pentadione or (R)-4,5-cyclohexylidenedioxy-2,3-pentadione (to yield DPD or ent-DPD, respectively). After sufficient hydrolysis has occurred, the method further comprises adjusting the pH to about neutral pH or a desired pH range, typically from about pH 7 to about pH 8.5, using a buffering agent suitable for storing DPD or for evaluating the bioactivity of DPD. Preferred pH ranges for evaluating bioactivity are from about pH 7 to about pH 7.5. For storage, the final pH is any value suitable for storing DPD. Stable DPD solutions can be obtained at acidic pH for DPD concentrations that range up to at least 100 mM and possibly higher, depending on the temperature of the solution. A preferred DPD concentration is 30 mM.

General Discussion of Synthetic Methods

Figure 2A:
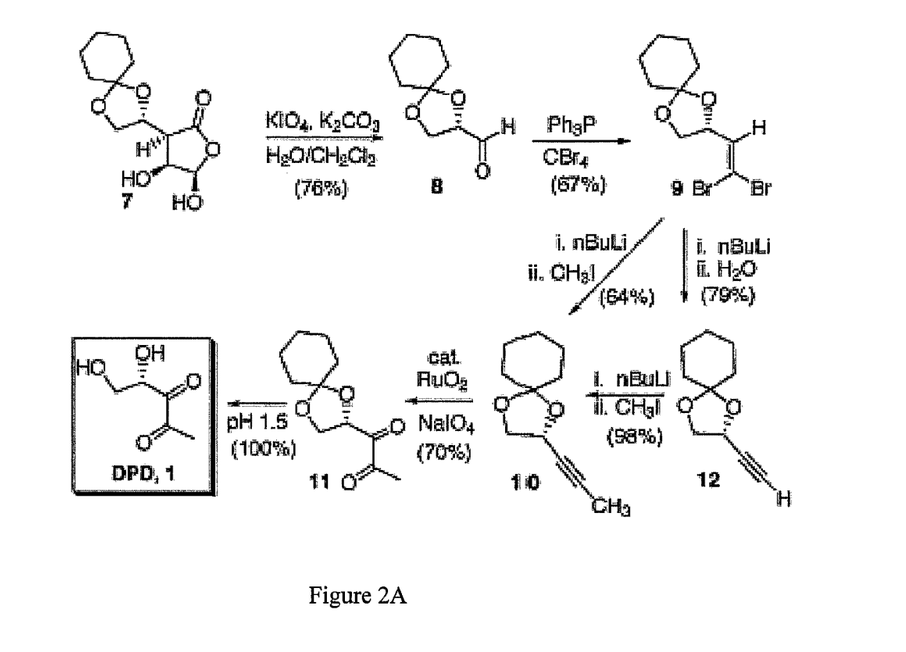
FIG. 2A shows the synthesis strategy for DPD.
Figure 2B:
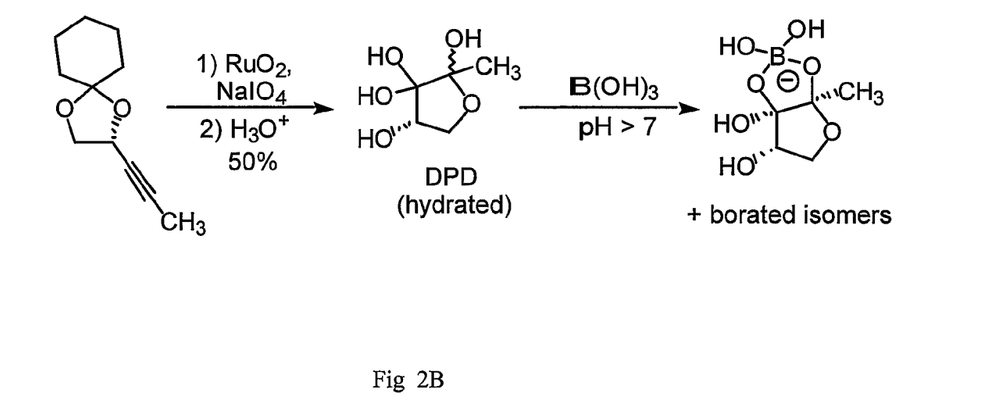
FIG. 2B illustrates the chemical reactions for 1) converting 10 to 11, and 2) the hydration step to obtain hydrated DPD (4 or 5). Hydrated DPD complexes (with borate) when present at pH>7 to produce 6 and borated isomers.

The synthesis strategy outlined in FIG. 2 constitutes an improvement of that recently reported by Meijler et al. (2004) for many reasons. The present invention employs different tactics that significantly improve the synthetic efficiency and make DPD readily available in multigram quantities. The previous synthesis of DPD made use of a labile methyl orthoester as a protecting group, which could be removed in dilute aqueous solution to produce DPD in situ for biological evaluation. The delicacy of that protecting group required that it be introduced at a late stage as a replacement for the acetonide group. However, this protection strategy led to complications with the oxidation to form the α-diketone (analog of 11; 10% yield). In addition, the acetonide series involves two intermediates of inconveniently high volatility.

With access to DPD prepared enzymatically (Schauder et al. 2001), the present invention establishes that DPD is stable at pH 1.5-2 in dilute aqueous solution for extended periods (no significant decrease in bioactivity after 16 h at 20° C. for concentrations of DPD at least of 30 mM and up to 100 mM). While enantio-pure glyceraldehyde equivalents provide a convenient conceptual starting point for the synthesis of DPD and other small molecules, the handling of these molecules can be difficult. Isopropylidene glyceraldehyde can be generated as either enantiomer in a few steps, but it is quite volatile and dimerizes readily (Grauert et al. 1985). These drawbacks have led to the development of other protecting groups for glyceraldehyde. For a general discussion, see: Schmid et al. 1992; for discussion and elaborate solutions, see: Michel et al. 2003 and Aube et al. 1992.

The cyclohexylidene group (FIG. 2A) offers lower volatility and efficient isolation, and can be removed rapidly at pH 1.3-1.5 and 20° C. Importantly, the cyclohexanone by product from deprotection does not inhibit cell growth at concentrations under 1 M. The monocyclohexylidene derivative (7) of L-gulonic acid γ-lactone was prepared in 75% yield as a white solid (Vekemans et al. 1985). Oxidative cleavage with $KIO_4$ led to aldehyde 8 (76%). Following a literature procedure (Yoshida et al. 1992), the Corey-Fuchs protocol gave rise to the dibromoalkene 9, which was purified (67% yield) prior to treatment with nBuLi; the intermediate alkyne anion was quenched with methyl iodide to give alkyne 10 in 64% yield after careful chromatography. Alternative quenching with water gave the alkyne 12 (79%); then methylation proceeded in 98% yield to 10. The critical oxidation process followed the protocol of Seebach (Zibuck et al. 1988) with $RuO_2/NaIO_4$ and produced the α-diketone 11 in 70% yield as a bright yellow crystalline solid. The yield is ca 20% overall from gulonic acid γ-lactone via 12. Compound II showed a strong tendency to hydrate at the C-3 carbonyl group to give 13 (FIG. 1B), which complicates the characterization. When 11 is placed in $H_2O$ or $D_2O$ at pH 1.5 and 20° C. at concentrations up to 30 mM, deprotection was >95% complete after 2.0 h with no detectable byproducts ($^1H$ NMR). After adjusting the buffer (0.5 M potassium phosphate, pH 7.3), synthetic DPD was observed to be equal in activity to enzymatically prepared DPD at equal concentration in the V. harveyi bioassay. Using this route, ent-DPD (14) and DPD labeled with $^{13}C$ at C-1 (15) were synthesized. Ent-DPD (14) had only 1% of the activity of DPD (1) in the V. harveyi bioassay.

Synthetically-produced DPD was stable under acidic conditions; a 30 mM sample of the molecule was monitored for decomposition via $^1H$ NMR for 5 h at 20° C. and pH 1.5. Under these conditions, no decomposition products were observed. A further examination of a 100 mM sample stored at 20° C. and pH 1.3 for 16 h showed no loss in activity as monitored by the V. harveyi bioassay. The purity of the synthetic DPD was further established by reaction with o-phenylenediamine to produce (S)-1-(3-methylquioxalin-2-yl)-ethane-1,2-diol in >98% purity.

DPD-Borate Binding Studies

Hydration of the carbonyl group at C-3 of the cyclic form (2) of DPD is important for borate binding in the V. harveyi signal, 6. Initially, it was not known whether hydration and subsequent borate addition were intrinsically favorable or required the presence of the protein receptor. For example, Pei and coworkers proposed that the C-3 carbonyl of DPD (enzymatically prepared) was hydrated in aqueous media (Zhu et al. 2003).

We showed that laurencione (FIG. 1B), which is 4-deoxy-DPD, hydrates spontaneously and associates strongly with borate in aqueous media at pH 7.8 (Semmelhack et al. 2004). It forms complexes with both 1:1 and 2:1 laurencione:borate stoichiometry. For synthetic DPD, the appearance of five $^{13}C$ NMR signals in the spectrum at pH 1.5 (30 mM DPD, aq) in the region from 90-110 ppm assigned to the hemiacetal and hydrated carbons strongly suggests that the majority of DPD, both open and closed isomers, is hydrated at C3. It is less stable at pH>8 unless bound to borate. Unlike laurencione, which is lacking the C-4 hydromyl group and therefore in the hydrated form contains only one site for borate complexation, hydrated DPD (4) has two sites for borate complexation. Since both 2,3- and 3,4-DPD borates are possible for each of the two anomers, a complex mixture of borate species is expected.

Figure 5:
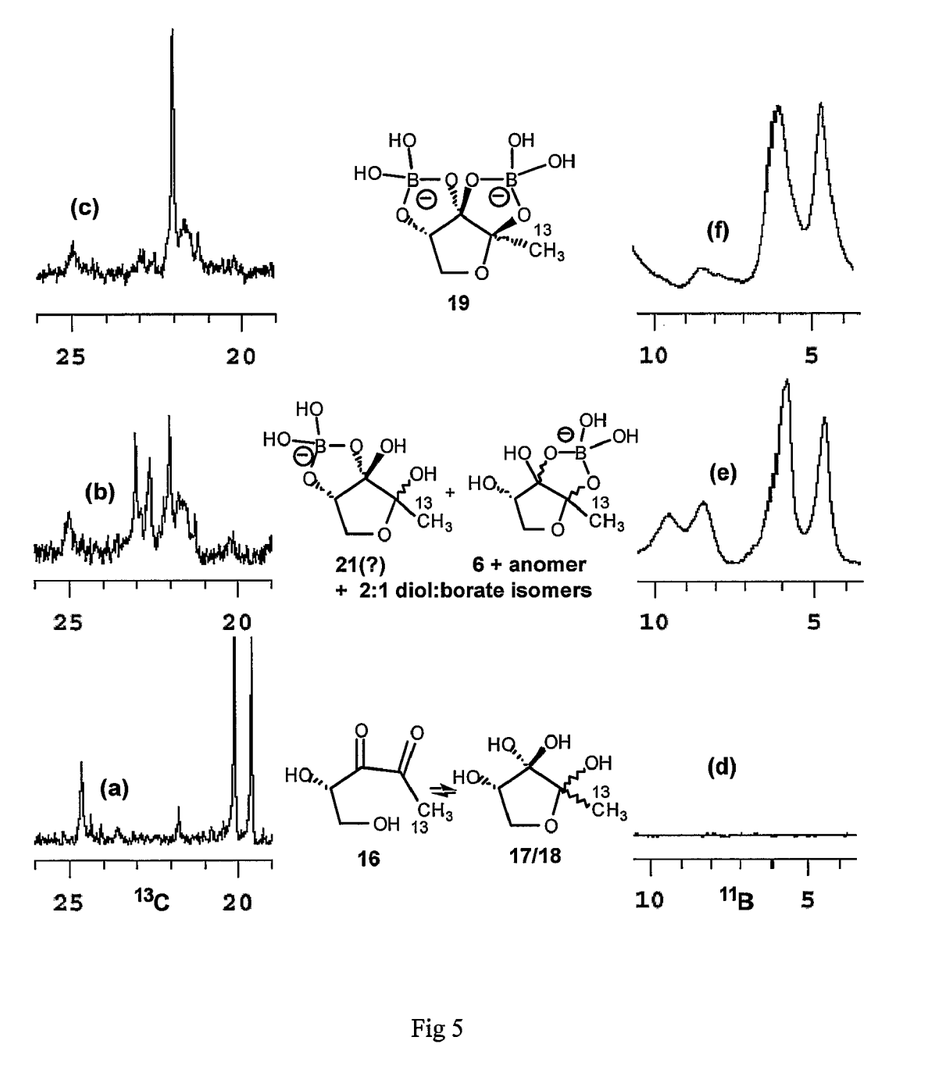
FIG. 5 shows $^{13}C$ NMR spectra (panels a-c) and $^{11}B$ NMR spectra (panels d-f) when 15 mM DPD is titrated with borate at pH 7.8. For the $^{13}C$ NMR titration: (a) no added $B(OH)_3$; (b) 45 mM $B(OH)_3$; (c) sat. $B(OH)_3$; for the $^{11}B$ NMR titration: (d) no added $B(OH)_3$; (e) 40 mM $B(OH)_3$; (f) sat. $B(OH)_3$.

Borate binding was followed with $^{13}C$-labeled DPD, 15, by both $^{11}B$ and $^{13}C$ NMR spectroscopy. As shown in FIG. 5A, in $H_2O$ (5% $D_2O$) and in the absence of borate, 15 mM 15 produces three main peaks from the incorporated label, assigned to the hydrated open form 16 (δ 24.9 ppm), and the two hydrated cyclic forms, 17/18 (δ 19.9 or 20.4 ppm). As borate is added, the complexity of the $^{13}C$ NMR spectrum increases, consistent with the hypothesis that a number of 1:1 and 2:1 DPD:borate complexes are present in solution; with 15 mM 15 and 45 mM $B(OH)_3$ (FIG. 5B) the signals for 16-18 are gone, confirming a high affinity of these isomers for boron. When the solution is saturated with boric acid (~0.9 M) and the concentration of 15 is kept at 15 mM, the $^{13}C$ NMR spectrum is dominated by a peak at δ 22.3 ppm to which we assign the 2:1 borate complex, 19 (FIG. 5C). Although 19 appears crowded and possesses two negatively charged groups, precedence for this structural type exists in work showing that small polyhydroxylated molecules can complex multiple tetrahedral phenyboranate ions in close proximity (Lorand et al. 1959).

When the identical titration is followed by $^{11}B$ NMR, no signal was observed initially with 15 mM 1 and no $B(OH)_3$ (FIG. 5D), but as the $B(OH)_3$ concentration was increased to 40 mM while holding the concentration of 1 constant (FIG. 5E), new peaks appeared: two broad peaks at δ 4.7 and 5.8 ppm and a family of peaks at δ 8-11 ppm (excessborate at δ 18.3 ppm not shown). The peak at δ 5.8 ppm is assigned to the natural product, 6 (and its anomer), based on analogy with 6 bound to the *V. harveyi* receptor LuxP (6.1 ppm) (Chen et al. 2002), 6 released from the LuxP receptor (δ 5.8 ppm) (Miller et al. 2004), 6 (δ 5.8 ppm) observed when 17 is released into borate from its receptor, LsrB, from *S. typhimurium* (Miller et al. 2004), and the 1:1 borate complex of laurencione (δ 5.9 ppm) (Semmelhack et al. 2004).

The peak at δ4.7 ppm is at a position typical of 1:1 sugar:borate complexes (Van Duin et al. 1985) and is tentatively assigned to the 3,4-borate complex, 21. The family of peaks from δ 8-11 ppm, have positions consistent with a mixture of 2:1 DPD:borate complexes (e.g, 20) with borate bound at either the 2,3 or 3,4 position (Semmelhack et al. 2004). As the concentration of borate is increased to saturation while keeping the concentration of 1 constant at 15 mM, the intensity of the peaks from δ 8-11 ppm decreases while the peaks at δ 4.7 and 5.8 ppm increase and become almost equal in intensity (FIG. 5F).

These data are consistent with the conversion of 2:1 DPD:borate complexes to 1:1 DPD:borate complexes (e.g., 6), followed by further conversion to 1:2 DPD:borate complex 19 as the borate concentration is increased. The inherently large number of borated DPD species formed coupled with the difficulties associated with accurately measuring the equilibrium constant for sugar borate binding (Springsteen et al. 2002) has not allowed quantitation of the equilibrium constant for the association of DPD with borate.

To explore the binding of DPD with borate under conditions that more closely resemble those in the natural habitat of *V. harveyi* and to correlate this study with previous work using DPD produced in vivo and released from the *V. harveyi* receptor protein, LuxP, the $^{11}B$ NMR spectrum of a 100 µM DPD solution in 400 µM $B(OH)_3$ (Dickson et al. 1990) at pH 7.5 was recorded. Under these conditions, one peak at δ 5.8 ppm corresponding to 1:1 DPD:borate complexes with borate bound at the 2,3-positions (6 and its anomer), was observed significantly above noise level. Based on the ratio of integrals for the $B(OH)_3$ peak and the DPD:borate peak, the concentration of DPD:borate complex was calculated to be ca 10 µM. consistent with ca 10% DPD bound at this dilution. We were unable to observe conclusively the presence of complexes with a 2:1 DPD:borate stoichiometry due to sensitivity limitations of the $^{11}B$ NMR experiment, although a peak with a S/N of 2 was recorded at δ 9.8 ppm.

Intermediates Compounds

Yet another aspect of the invention provides compounds useful as intermediates in the synthesis of DPD, new borate isomers as well as the isotopically labeled DPD compounds (including the isomeric forms of the isotopically-labeled DPD). These compounds are those shown as compounds 10, 11, 12, 15, 16, 17, 18, 19, 20 and 21 in FIGS. 1B and 2A. Where possible, the invention includes the pharmaceutically-acceptable salts of these compounds.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues and the like. Pharmaceutically acceptable salts include, but are not limited to, hydrohalides, sulfates, methosulfates, methanesulfates, toluenesulfonates, nitrates, phosphates, maleates, acetates, lactates and the like.

Pharmaceutically-acceptable salts of the compounds of the invention can be prepared by reacting the free acid or base forms of these compounds with a stoichiometric or greater amount of the appropriate base or acid in water or in an organic solvent, or in a mixture of the two; generally, non-aqueous media like ether, ethyl acetate, ethanol, isopropanol, or acetonitrile are preferred. The salts of the invention can also be prepared by ion exchange, for example. Lists of suitable salts are found in Remington's Pharmaceutical Sciences, 17th ed., Mack Publishing Company, Easton, Pa., 1985, p. 1418, the disclosure of which is hereby incorporated by reference in its entirety.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

EXAMPLE 1

General Procedures

A. General. Unless otherwise rioted, all reactions were performed under an inert atmosphere with dry reagents, solvents, and flame dried glassware. Reagents were purchased from Acros, Aldrich, or Fluka and used without further purification. With the exception of $CH_3I$, which was distilled before use. Silica flash chromatography was performed using silica gel α, 230×540 mesh (SORBENT Technologies). Analytical thin layer chromatography was performed using Silica G TLC plate, w/UV254, 200 µm (SORBENT Teclhnologies). The $^1H$ NMR spectra were recorded using a Varian Mercury (300 MHz), Varian Unity (400 MHz), or Varian Unity/INOVA (500 MHz) spectrometer, and $^{13}C$ NMR spectra were recorded using a Varian Unity/INOVA (125.7 MHz) spectrometer. Chemical shifts for $^1H$ and $^{13}C$ NMR spectra are reported in parts per million (ppm) on the δ scale from an internal standard, except for $^{13}C$ NMR recorded in $D_2O$ which were referenced to an external standard. The $^{11}B$ NMR spectra were collected at 20° C. using a Varian Unity/INOVA spectrometer at 160.5 MHz equipped with a 5-rnm tunable X/$^1H$ probe (Nalorac), and were referenced indirectly to $BF_3.Et_2O$. A collection of 3072 scans was averaged for each $^{11}B$ spectrum with a 0.25-s recycle time using an approximately 30° flip-angle pulse. Specific rotations were measured on a PerkinElmer Model 341 Polarimeter using an average of 20 readings for each measurement. High resolution mass spectra were recorded using a Kratos MS 50 RFA.

In the reactions below that indicate preparation of both the L- and D-forms of the compounds, stereoselective synthesis is obtained using the appropriate enantiomer as the starting material or using the stereospecific reaction product from the previous step in the synthesis pathway. For example, in Example 2, starting with L-gulonic acid-γ-lactone yields the final product in its L-form and starting with D-gulonic acid-γ-lactone yields the final product in its D-form.

B. Nomenclature. As shown in FIG. 1A, DPD spontaneously cyclizes to form two epimeric furanoses, (2S,4S)- and (2R,4S)-2,4-dihydroxy-2-methyldihydrofuran-3-one (S- and R-DHMF, respectively; also 2 and 3, respectively). Hydration of S- and R-DHMF gives rise to (2S,4S)- and (2R,4S)-2-methyl-2,3,3,4-tetrahydroxytetrahydrofuran (S- and R-THMF, respectively; also 4 and 5, respectively).

The IUPAC carbohydrate nomenclature for the structures in FIG. 1A is as follows: DPD, 1, L-glycero-1-dehydro-penta-2,3-diulose; S-DHMF, 2, α-L-glycero-1-dehydro-penta-2,3-diulo-2,5-furanose; S-THMF, 4,α-L-glycero-1-dehydro-3-hydro-penta-2,3-diulo-2,5-furanose; S-THMF-borate, 6,α-L-glycero-1-dehydro-3-hydro-penta-2,3-diulo-2,5-furanosyl-2,3-cyclicborate; R-DHMF, 3, β-L-glycero-1-dehydro-penta-2,3-diulo-2,5-furanose; and R-THMF, 5, β-L-glycero-1-dehydro-3-hydro-penta-2,3-diulo-2,5-furanose.

EXAMPLE 2

Preparation of 5,6-O-Cyclohexylidene-L or D-gulono-1,4-lactone, 7 or ent-7

To a slurry of gulonic acid-γ-lactone (20.02 g, 112.4 mmol) and p-toluene sulfonic acid monohydrate (203 mg, 1.1 mmol) in DMF (100 mL) was added 1,1-dimethoxy cyclohexanone (28.1 g, 29.6 mL, 194.9 mmol) in one portion. The resulting mixture was stirred until the reaction was homogeneous (36-48 h). Et$_3$N (0.8 mL) was added and stirring was continued for 1 h. The reaction was then concentrated at α° C. in vacuo (0.5 mmHg). Addition of PhMe (250 mL) to the warm suspension followed by cooling at −20° C. for 24 h yielded the product as a white precipitate. The precipitate was collected via filtration, washed with PhMe, and dried in vacuo (0.5 mmHg) for 24 h at room temperature to give 7 (21.65 g, 75% yield). The resulting material contained 5% starting material and ~1% solvent and was used in subsequent reactions without further purification. $^1$H NMR (300 MHz, DMSO-d): δ 5.59 (d, J=7.5 Hz, 1H), 5.46 (d, J=4.2 Hz, 1H), 4.42 (dd, J=4.6, 7.5 Hz, 1H), 4.22 (m, 3H), 4.13 (m, 1H), 3.76 (m, 1H), 1.54 (m, 8H), 1.35 (m, 2H). [Vekerans et al. 1985.]

EXAMPLE 3

Preparation of 2,3-O-Cyclohexylidene-L or D-glyceraldehyde, 8 or ent-8

To a slurry of KIO$_4$ (10.093 g, 43.90 mmol) and KHCO$_3$ (9.053 g, 90.50 mmol) in H$_2$O (28 mL) was added 7 (5.050 g, 19.60 mmol). CH$_2$Cl$_2$ (50 mL) was added, and the resulting two-phase mixture was stirred vigorously for 18 h in air. At this time, the mixture was diluted with CH$_2$Cl$_2$ (50 mL), and aqueous NaCl (~0.8 g/mL H$_2$O) was added. Stirring was continued until the aqueous layer gelled. The reaction was filtered, and the residue was washed with CH$_2$Cl$_2$ (2×50 mL). The eluant was collected and washed with H$_2$O (50 mL). The aqueous fractions were combined and extracted with CH$_2$Cl$_2$ (2×25 mL). The combined organic fractions were dried with MgSO$_4$ and concentrated in vacuo giving 8 (2.525 g) in 76% yield and >95% purity. The aldehyde was used without further purification. Due to ABX second order effects, the coupling constants are only reported as 1D approximations. $^1$H NMR (300 MHz, CDCl$_3$): δ 9.73 (d, J=1.9 Hz, 1H), 4.39 (ddd, J=1.9, 4.7, 7.3 Hz, 1H), 4.18 (dd, J=7.3, 8.8 Hz, 1H), 4.10 (dd, J=4.7, 8.8 Hz, 1H), 1.65 (m, 8H), 1.44 (m, 2H). [Previously characterized by Grauert et al. 1985.]

EXAMPLE 4

Preparation of (R or S)-1,1-Dibromo-3,4-cyclohexylidenedioxybut-1-ene, 9 or ent-9

Triphenyl phosphine (9.181 g, 35.00 mmol) was dissolved in CH$_2$Cl$_2$ (85 mL) and cooled to 0° C. To the cooled solution was added CBr$_4$ (5.851 g, 17.60 mmol) all at once, and the mixture was stirred for 1 h. At this time a solution of 8 (2.525 g, 14.90 mmol) in 20 mL CH$_2$Cl$_2$ was added in one portion, and the mixture was stirred for 1 h. The solution was concentrated in vacuo, and the residual solid was purified via column chromatography (SiO$_2$ eluted with 1:9 EtOAc:hexanes) to give 9 (3.268 g ,67% yield). R$_f$=0.83 (1:1, EtOAc:hexanes). $^1$H NMR (300 MHz, CDCl$_3$): δ 6.54 (d, J=7.7 Hz, 1H), 4.74 (ddd, J=6.3, 6.5, 7.7 Hz, 1H), 4.19 (dd, J=6.3, 8.4 Hz, 1H), 3.69 (dd, J=6.5, 8.4 Hz, 1H), 1.63 (m, 8H), 1.42 (m, 2H).

[Previously characterized by Yoshida et al. 1992.]

EXAMPLE 5

Preparation of (R or S)-1,2-Cyclohexylidenedioxypent-3-yne, 10 or ent-10

Dibromoalkene, 9 (1.019 gm 3.10 mmol) was dissolved in THF (20 mL) and subsequently cooled to −78° C. To this solution was added a solution of nBuLi (2.5 M in hexanes, 3.0 mL, 7.5 mmol) over 15 min via an addition funnel. The reaction was allowed to proceed at −78° C. for an additional 30 min. At this time, the solution was warmed to 23° C. and stirred for 1 h. Then, CH$_3$I (580 µL, 1.32 g, 9.30 mmol) was added, and stirring was continued for 3 h. The mixture was cooled to 0° C., quenched with H$_2$O (100 µL), dried with MgSO$_4$, filtered, and concentrated in vacuo. Purification via chromatography (SiO$_2$ eluted with 0.5:9.5 Et$_2$O:hexanes) gave 10 (358 mg) in 64% yield. R$_f$=0.64 (0.5:9.5, Et$_2$O:hexanes). IR (NaCl) ν$_{max}$(cm$^{-1}$): 2936 (s, C—H), 2862 (s, C—H), 2242 (w, C≡C), 1163 (m, C—O), 1105 (s, C—O). 10 [α]$_D^{20}$ −39.2° (c 0.767, CHCl$_3$). $^1$H NMR (500 MHz, CDCl$_3$): δ 4.67 (ddd, J=7.0, 6.1, 2.1 Hz, 1H), 4.10 (dd, J=7.9, 6.1 Hz, 1H), 3.81 (dd, J=7.0, 7.9, 1H), 1.84 (d, J=2.1 Hz, 3H), 1.77 (m, 2H), 1.61 (m, 6H), 1.39 (m, 2H). $^{13}$C NMR (125.7 MHz, CDCl$_3$): δ 110.7, 82.5, 76.5, 69.9, 65.7, 36.0, 35.6, 25.2, 24.1, 25.2, 24.1, 24.0, 3.7. HRMS (m/z): M+calcd. For C$_{11}$H$_{16}$O$_2$, 180.115; found, 179.635.

The same procedure produced Ent-10: [α]$_D^{20}$ +39.4° (c 0.796, CHCl$_3$).

EXAMPLE 6

Preparation of (R)-1,2-Cyclohexylidenedioxybut-3-yne, 12

Vinyldibromide, 9 (1.209 g, 3.70 mmol) was dissolved in THF (20 mL) and subsequently cooled to −78° C. To this solution was added a solution of nBuLi (2.5 mL in hexanes, 3.6 mL, 9.0 mmol) over 15 min via an addition funnel. The reaction was allowed to proceed at −78° C. for 30 min. At this time, the solution was warmed to 23° C. and stirred for 1 h. The mixture was then cooled to 0° C., quenched with H$_2$O (100 µL), dried with MgSO$_4$, filtered, and concentrated in vacuo. Purification via chromatography (SiO$_2$ eluted with 0.5:9.5 Et$_2$O:hexanes) gave 12 (485 mg, 79% yield). R$_f$=0.65 (0.5:9.5, Et$_2$O:hexanes). $^1$H NMR (500 MHz, CDCl$_3$): δ 4.71 (ddd, J=6.5, 6.3, 2.0 Hz, 1H), 4.17 (dd, J=8.0, 6.5 Hz, 1H), 3.95 (dd, J=8.0, 6.3 Hz, 1H), 2.49 (d, J=2.0 Hz, 1H), 1.76 (m, 2H), 1.63 (m, 6H), 1.42 (m, 2H). [Previously characterized by Yoshida et al. 1992.]

EXAMPLE 7

Preparation of (R)-1,2-Cyclohexylidenedioxypent-3-yne-($^{13}$C$_5$), 10-($^{13}$C$_5$)

To a solution of 12 (175 mg, 1.10 mmol) in THF (1.6 mL) at −78° C. was added a solution of nBuLi (2.5 M in hexane, 550 μL, 1.40 mmol) in one portion, and the mixture was allowed to stir for 30 min. At this time, $^{13}$CH$_3$I (308 mg, 135 μL, 2.20 mmol) was added, and the mixture was allowed to warm to 23° C. and be stirred for 4 h. The reaction was then cooled to 0° C. and quenched with H$_2$O (20 μL). Drying with MgSO$_4$, followed by concentration in vacuo, and filtration through silica using 1:2 Et$_2$O:hexanes as the eluant afforded pure 10-($^{13}$C$_5$) (186 mg) in 98% yield. $^1$H NMR (500 MHz, CDCl$_3$): δ 4.67 (ddd, J=7.0, 6.1, 2.1 Hz, 1H), 4.10 (dd, J=7.9, 6.1 Hz, 1H), 3.81 (dd, J=7.0, 7.9, 1H), 1.84 (dd, J=131.5, 2.1 Hz, 3H), 1.77 (m, 2H), 1.61 (m, 6H), 1.39 (m, 2H). $^{13}$C NMR (125.7 MHz, CDCl$_3$): δ 110.7, 82.5 (d, $^1$J$_{(C1)(C2)}$=67.8 Hz), 76.5 (d, $^2$J$_{(C1)(C3)}$=11.2 Hz), 69.9, 65.7, 36.0, 35.6, 25.2, 24.1, 25.2, 24.1, 24.0, 3.7.

EXAMPLE 8

Preparation of (S or R)-4,5-Cyclohexylidenedioxy-2,3-pentadione, 11 or ent-11

To a solution of 10 (330 mg, 1.8 mmol) in CCl$_4$ (4 mL) and MeCN (4 mL) was added NaIO$_4$ (867 mg, 4.1 mmol) in H$_2$O (6 mL). The mixture was vigorously stirred, and RuO$_2$.H$_2$O (6.0 mg, 4.5×10$^{-2}$ mmol) was added. The mixture was vigorously stirred for 15 min in air. At this time, it was filtered through silica using CH$_2$Cl$_2$ as the eluant. The eluant was dried with MgSO$_4$ and concentrated in vacuo to give a bright yellow oil. Purification via flash chromatography using SiO$_2$ eluted with 1:9 EtOAc:hexanes afforded pure 11 (271 mg) in 70% yield with varying amounts of C3 hydration, i.e. 13 (~10-30%). IR (NaCl) ν$_{max}$ (mixture of 11 and 13) (cm$^{-1}$): 3447 (w, br, OH),2937 (s, CH), 2863 (m, CH), 1794 (w, C═O, hydrated diketone), 1733 (s, C═O, diketone), 1714 (s, C═O, diketone), 1162 (m, C—O), 1145 (m, C—O), 1093 (s, C—O). Azeotropic drying of the oil with CHCl$_3$ produced a yellow solid that contained >95% 11. R$_f$=0.1-0.3 (1:9 EtOAc: hexanes). [α]$_D^{20}$-11.8° (c 0.900, CHCl$_3$). HRMS (m/z): M$^+$ calcd. For C$_{11}$H$_{16}$O$_4$, 212.105; found, 212.645.

In CDCl$_3$, 11 was characterized with <5% 13. $^1$H NMR (500 MHz, CDCl$_3$) (11): δ 5.14 (dd, J=5.2, 7.9 Hz, 1H), 4.35 (dd, J=7.9, 8.9 Hz, 1H), 4.00 (dd, J=5.2, 8.9 Hz, 1H), 2.40 (s, 3H), 1.64 (m, 8H), 1.42 (m, 2H). $^{13}$C NMR (125.7 MHz, CDCl$_3$) (11): δ 198.2, 194.9, 111.9, 76.5, 65.5, 35.4, 34.7, 25.0, 24.5, 23.82, 23.77.

In aqueous (D$_2$O) solution, 13 formed in >95%, as evidenced by the presence of a new peak at δ 95.7 ppm in the $^{13}$C NMR spectrum, and the presence of only one peak in the carbonyl region (δ 210.2 ppm). Further evidence for the position of hydration is provided as part of the analytical data for 11/13-($^{13}$C$_1$). $^1$H NMR (500 MHz, D$_2$O, 13): δ 4.43 (dd, J=5.3, 7.2 Hz, 1H), 4.14 (dd, J=7.2, 9.0 Hz, 1H), 4.05 (dd, J=5.3, 9.0 Hz, 1H), 2.36 (s, 3H), 1.67-1.30 (m, 10H). $^{13}$C NMR (125.7 MHz, D$_2$O, 13): δ 210.2, 112.1, 95.7, 77.1, 63.8, 34.9, 33.2, 25.1 (splitting due to D exchange was noted), 24.5, 23.6, 23.3. Due to the long exposure to D$_2$O necessary to obtain the $^{13}$C NMR spectrum, partial deprotection of the molecule occurred. The weak additional peaks in the $^{13}$C NMR spectrum (below) of 13 in D$_2$O at δ 42.0 and 27.0 ppm are due to small amounts of cyclohexanone.

If 11 is dissolved in D$_2$O and then extracted into CDCl$_3$, 22 95% 13 could be initially characterized in organic solvent as evidenced by $^1$H NMR. However,13 converts to 11 with a t$_{1/2}$ of 13 h at 20° C. $^1$H NMR (500 MHz, CDCl$_3$, 13): δ 4.26 (dd, J=5.5, 6.7 Hz, 1H), 4.129 (d, J=5.5 Hz, 1H), 4.127 (d, J=6.7 Hz, 1H), 2.42 (s, 3H), 1.71-1.56 (m, 8H), 1.41 (m, 2H). $^{13}$C NMR (125.7 MHz, CDCl$_3$, 13): (reporting only peaks corresponding to 13): δ 206.3, 111.2, 94.6, 76.6, 64.6, 35.8, 25.0, 24.5, 24.1, 23.9, 23.7. Due to the length of observation necessary to fully develop the $^{13}$C spectrum of 13, considerable dehydration was observed along with deprotection. Therefore, the $^{13}$C NMR spectrum in CDCl$_3$ of 13 (below) also contains peaks attributed to 11 and cyclohexanone.

Ent-11 [α]$_D^{20}$+11.5° (c 0.733, CHCl$_3$).

EXAMPLE 9

Preparation of (S)-4,5-Cyclohexylidenedioxy-2,3-pentadione-($^{13}$C$_1$), 11-($^{13}$C$_1$)

Protected DPD, 11, $^{13}$C labeled at the C1 position (42 mg, 44% yield) was obtained from 10-($^{13}$C$_1$) (81 mg,0.4 mmol) using the procedure for 11. $^1$H NMR (500 MHz, CDCl$_3$): δ 5.14 (dd, J=5.2, 7.9 Hz, 1H), 4.35 (dd, J=7.9, 8.9 Hz, 1H), 4.00 (dd, J=5.2, 8.9 Hz, 1H), 2.40 (d, J=129.4 Hz, 3H), 1.64 (m, 8H), 1.42 (m, 2H). $^{13}$C NMR (125.7 MHz, CDCl$_3$): δ 198.2 (d, $^1$J$_{(C1)(C2)}$=42.6 Hz), 194.9 (d, $^2$J$_{(C1)(C3)}$=12.4), 111.9, 76.5, 65.5, 35.4, 34.7, 25.0, 24.5, 23.82, 23.77. $^1$H NMR (500 MHz, D$_2$O): δ 4.43 (dd, J=5.3, 7.2 Hz, 1H), 4.14 (dd, J=7.2, 9.0 Hz, 1H), 4.05 (dd, J=5.3, 9.0 Hz, 1H), 2.36 (d, J=128.4 Hz, 3H), 1.67-1.30 (m, 10H). $^{13}$C NMR (125.7 MHz, 0.5:9.5 D$_2$O:H$_2$O): δ 210.2 (d, $^1$J$_{(C1)(C2)}$=41.2), 112.1, 95.7 (d, $^2$J$_{(C1)(C3)}$=11.4), 77.1, 63.8, 34.9, 33.2, 25.1, 24.5, 23.6, 23.3.

The position of hydration in the molecule in aqueous media was confirmed by $^{13}$C NMR analysis. The peak at δ 95.7 ppm in the $^{13}$C NMR spectrum for 11-($^{13}$C$_1$) in 5% D$_2$O in H$_2$O displayed two bond C—C coupling (11.4 Hz) with the $^{13}$C label at C1. The chemical shift is also in the range noted for hydrated carbonyl groups. Taken together, these data are consistent with hydration at C3. Two new peaks at δ 24.6 and 22.3 ppm were also observed in the $^{13}$C spectrum of 11-($^{13}$C$_1$) in 5% D$_2$O (spectrometer lock signal) in H$_2$O, but not in the $^{13}$C spectrum of 11 in D$_2$O. These peaks are assigned to the methyl carbon for small amounts of unhydrated and C2 hydrated material that are only detectable with $^{13}$C incorporation. The two new peaks also show splitting due to D exchange if the $^{13}$C spectrum is recorded in 100% D$_2$O.

EXAMPLE 10

Procedure for Initial Characterization of 4,5-dihydroxy-2,3-pentadione, 1

To a suspension of 11 (14 mg, 6.6 mmol) in D$_2$O (3.2 mL) was added conc. H$_2$SO$_4$ (4 μL, ca pH 2). The reaction was allowed to continue for 2.5 h and was monitored by $^1$H NMR. Deprotection was determined to be ~90% complete after 1.5 h and greater than ~97% complete after 2.5 h. At this time, excess NaHCO$_3$ and excess B(OH)$_3$ were added to generate a solution of excessborate at pH 7.8. This solution was active in the *V. harveyi* autoinducer-bioassay without further purification. Before addition of NaHCO$_3$ and B(OH)$_3$, a 1 mL aliquot of the material showed an $^1$H NMR spectrum consistent with previously reported data. $^1$H NMR (500 MHz, D$_2$O, pD=2.0): δ 4.36 (dd, J=5.6, 7.0 Hz, 1H), 4.17 (m, 2H), 4.03 (dd, J=3.2, 5.9 Hz, 1H), 3.96 (dd, J=3.8, 7.3 Hz, 1H), 3.80 (m, 2H), 3_63 (dd, J=7.3, 12.0 Hz, 1H), 3.56 (dd, J=5.6, 9.4 Hz, 1H) [The previously reported peak at 2.35 (s, 3H) corresponding to the methyl protons of the ring open isomer was obscured by cyclohexanone.], 1.42 (s, 3H), 1.40 (s, 3H). [Previously partially characterized by Meijler et al. 2004.]

EXAMPLE 11

Procedure for $^1$H-NMR Characterization of 4,5-dihydroxy-2,3-pentadione, 1

To a suspension of 11 (9.6 mg, 30 mmol) in D$_2$O (1.5 mL) was added conc. D$_2$SO$_4$ (1.5 μL, final pD1.5). The reaction was allowed to continue for 5 h and was monitored by $^1$H NMR. A $^1$H-$^1$H DQCOSY spectrum was recorded at the 5-h time point to help establish the identity of each $^1$H signal. These data are consistent with previous assignments (Janda et al.). $^1$H NMR (500 MHz, D$_2$O, pD=1.5, 5 h): δ 4.36 (dd, J=5.6, 7.0 Hz, 1H), 4.17 (m, 2H), 4.03 (dd, J=3.2, 5.9 Hz, 1H), 3.96 (dd, J=3.8, 7.3 Hz, 1H), 3.80 (m, 2H), 3.63 (dd, J=7.3, 12.0 Hz, 1H), 3.56 (dd, J=5.6, 9.4 Hz, 1H), previously reported peak at 2.35 (s, 3H) corresponding to the methyl protons of the ring open isomer obscured by cyclohexanone, 1.42 (s, 3H), 1.40 (s, 3H). The extra signals in the region form 1.35-1.45 ppm and 3.4-4.6 ppm are most likely due to a small amount of 1 that is not hydrated at C3. This hypothesis is supported by the complete disappearance of these peaks upon addition of 1,2-phenylenediamine (see Example 13)

EXAMPLE 12

Procedure for $^{13}$C NMR Characterization of 4,5-dihydroxy-2,3-pentadione, 1

To a suspension of 11 (4.5 mg, 30 mmol) in H$_2$O (0.665 mL) and D$_2$O (0.035 mL) was added conc. D$_2$SO$_4$ (1.5 mL, final pD 1.5). The reaction was allowed to continue for 2.5 h. At this time the $^{13}$C NMR spectrum was recorded. $^{13}$C NMR (125.7 MHz, 95:5 H$_2$O:D$_2$O, PH 1.5): ring open isomer (C2 carbonyl not observed): δ 24.9, 61.8, 74.3, 97.2; cyclic isomers: δ 19.9, 20.4, 69.4, 71.3, 73.8, 74.6, 99.4, 99.7, 103.9, 104.7. Note, peaks at δ 24.6, 27.3, 41.9, 221.2 correspond to cyclohexanone. The appearance of 4 $^{13}$C NMR signals that can be attributed to the ring closed isomers in the region from 90-110 ppm (consistent with signals from hemiacetal and hydrated carbons) strongly suggest that the majority of DPD is hydrated at C3 under the above experimental conditions.

EXAMPLE 13

(S)-1-(3-methylquinoxalin-2-yl)-ethane-1,2-diol

To a suspension of 11 (9.6 mg, 30 mmol) in D$_2$O (1.5 mL) was added conc. D$_2$SO$_4$ (1.5 μL, final pD 1.5), and the reaction was allowed to continue for 5 h. At this time, 400 μL of the solution containing 11 was mixed with 100 μL of a solution of 1,2-phenylenediamine dihydrochloride (17.9 mg, 200 mM) in D$_2$O (0.5 mL). The resulting solution, containing 24 mM DPD and 40 mM phenylenediamine, was allowed to stand at room temperature for 40 min. The conversion of DPD to (S)-1-(3-methylquinoxalin-2-yl)-ethane-1,2-diol was judged to be >97% via $^1$H NMR. Of interest is the absence of $^1$H NMR signals in the region from 3.4-4.6 ppm that could be attributed to DPD or a large amount of by-product. $^1$H NMR (500 MHz, D$_2$O, pD=1.5, 5 h): δ 8.31 (m, 1H), 8.14 (m, 1H), 5.42 (dd, J=4.6, 6.4 Hz, 1H), 4.05 (dd, J=4.6, 12.0 Hz, 1H), 4.00 (dd, J=6.4, 12.0 Hz, 1H), 3.02, (s 3H).

EXAMPLE 14

Production of (S or R)-4,5-Dihydroxy-2,3-pentadione, 1, Suitable for Storage and Biological Evaluation To a suspension of 11 (10 mM) in H$_2$O (5 mL) was added conc. H$_2$SO$_4$ (5 μL). The reaction was allowed to continue for 2 h. At this time, the mixture was diluted with 1 M potassium phosphate buffer (5 mL) to adjust the pH to 7.3, yielding 5 mM DPD, 1, in 0.5 M potassium phosphate buffer. This material could be used without further purification in the *V. harveyi* bioassay, and displayed an activity equal to that of enzymatically prepared DPD (See next Example).

EXAMPLE 15

Bioassay Procedure

*V. harveyi* strain MM32 (luxN$^-$ luxS$^-$) was grown overnight and subsequently diluted 5.000-fold in AB growth medium. This bioassay was performed as developed by the method of Schauder et. al. (2001). To 90 μL of diluted cells ,10 μL of various compounds were added, and the resulting cultures were further incubated in a 96-well microtiter dish at 30° C. for approximately 6 h. The concentration of crude DPD was calculated by measuring the amount of homocysteine released in an Ellman's test. Light emission was measured using a Wallac model 1450 microbeta Plus scintillation counter.

Figure 3:
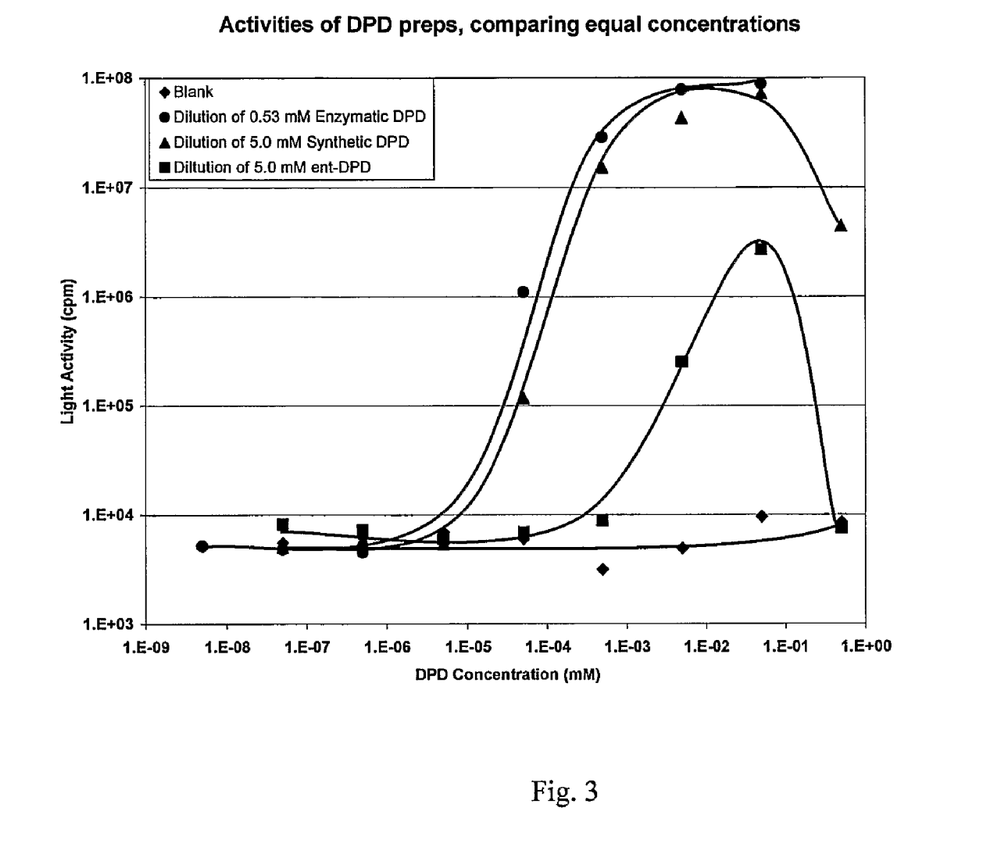
FIG. 3 shows the comparative bioactivity of enzymatically-produced DPD, synthetic DPD and synthetic ent-DPD.

A. Comparative bioactivity of enzymatically-produced DPD, synthetic DPD and synthetic ent-DPD. Each of these three compounds and a blank were assessed in the above bioassay at equal concentrations. The bio assays were conducted with a dilution of 0.53 mM enzymatically-produced DPD, a dilution of 5.0 mM synthetic DPD or a dilution of 5.0 mM ent-DPD. The results are shown in FIG. 3.

Figure 4A:
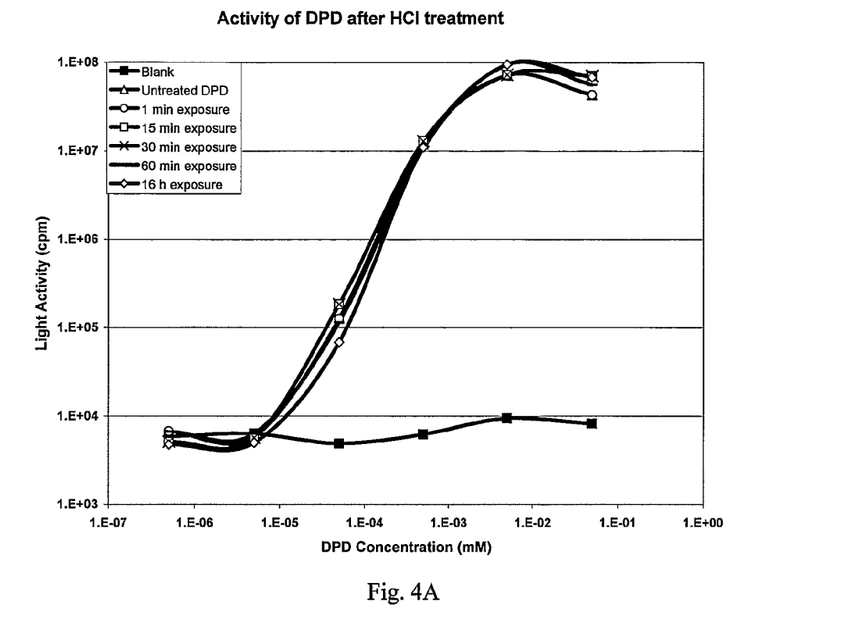
FIG. 4A shows the effects of low pH on enzymatically-produced DPD.

B. Effects of low pH on enzmmatically-produced DPD bioactivity. Enzymatically produced DPD (0.53 mM stock concentration) was mixed with sulfuric or hydrochloric acid at a ratio of 1 μL H$_2$SO$_4$ or 5 μL HCl to 250 μL DPD, resulting in solutions with a pH of 1.5 (with H$_2$SO$_4$) or 2 (with HCl). At times indicated, 1 M Tris pH 8.5 was added to restore the pH to neutral and bioactivity was determined. FIG. 4A shows the results after exposure to HCl treatment. Similar results were obtained after exposure to H$_2$SO$_4$ (not shown). Treatment of enzymatically-produced DPD with acid for up to 16 h did not affect the autoinducer activity.

Figure 4B:
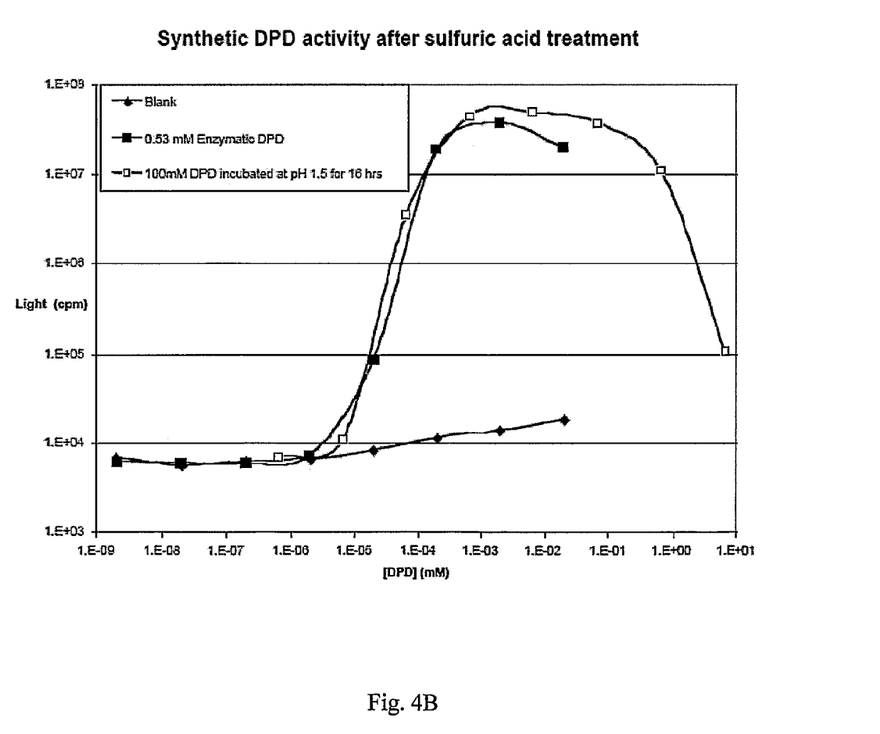
FIG. 4B shows the effects of low pH on synthetic DPD.

C. Effects of low pH on synthetic DPD bioactivity. Synthetically-produced DPD (100 mM stock concentration) was mixed with H$_2$SO$_4$ at a ratio of 1 μL H$_2$SO$_4$ to 250 μL DPD, resulting in solutions with a pH of 1.3. After 16 h, 1 M Tris pH 8.5 was added at a ratio of 5 μL buffer to 20 uL DPD solution to restore the pH to 7.5. This bioassay carried out as before shows that after treatment of synthetic DPD at a concentration of 100 mM and pH 1.3 for up to 16 h did not change the auto inducer activity (FIG. 4B).

EXAMPLE 16

$^{13}C$ NMR DPD-Borate Binding Study Using DPD-($^{13}C_1$), 15

To a suspension of 11-($^{13}C_1$) (5.2 mg, 0.025 mmol) in 0.5:9.5 $D_2O:H_2O$ (1.64 mL) was added conc. $H_2SO_4$ (2 μL). The reaction was allowed to continue for 2.0 h, and the $^{13}C$ NMR shifts for the methyl groups of the equilibrium mixture were recorded. Excess $NaHCO_3$ and $B(OH)_3$ (4.6 mg, 0.074 mmol) were added to generate a sat. $NaHCO_3$ and 45 mM $B(OH)_3$ solution (pH 7.8), and the $^{13}C$ NMR spectrum of the resulting mixture was recorded. Excess $B(OH)_3$ was added to the mixture to generate a sat. $B(OH)_3$ solution, and the sample was further analyzed via $^{13}C$ NMR spectroscopy. The results are shown in FIG. 5A-C and discussed in the Detailed Description of the Invention.

EXAMPLE 17

$^{11}B$ NMR DPD-Borate Binding Study

To a suspension of 11 (8.1 mg, 0.038 mmol) in 0.5:9.5 $D_2O:H_2O$ (1.53 mL) was added conc. $H_2SO_4$ (2 μL). The deprotection was allowed to continue for 2 h. At this time, excess $NaHCO_3$ was added to generate a sat. $NaHCO_3$ solution (pH 7.8). The material was divided into aliquots, and 100 mM $B(OH)_3$ in sat $NaHCO_3$ (aq) and sat $NaHCO_3$ (aq) were added in various proportions to generate 15 mM DPD in 5 mM, 15 mM, and 40 mM $B(OH)_3$ solutions with final volumes of 0.5 mL. These solutions were studied by $^{11}B$ NMR. Excess $B(OH)_3$ was added to the 45 mM $B(OH)_3$ sample to generate a saturated $B(OH)_3$ solution, and this sample was subjected to further $^{11}B$ NMR analysis. The results are shown in FIG. 5D-F and discussed in the Detailed Description of the Invention.

To explore further the ability of DPD to complexborate at more physiologically relevant concentrations, a mixture of 10 μL of 40 mM $B(OH)_3$, 101 L of 10 mM DPD, 100 μL of 1 M potassium phosphate buffer (pH 7), 200 μL of sat. $NaHCO_3$ and 680 μL of $D_2O$ was produced to generate a 100 μM DPD solution in 400 μM $B(OH)_3$, at pH 7.5. This solution was then analyzed by $^{11}B$ NMR to determine binding, as discussed in the Detailed Description of the Invention.

REFERENCES

Aube, J. et al. (1992) *Tetrahedron* 48, 45, 9819-9826.
Chen, X. et al. (2002) *Nature* 415, 545-549.
Cornell, K. A. et al. (1998). *Biochim. Biophys. Acta* 1396, 8-14.
Dickson, A. G. (1990) *Deep-Sea Research* 37, 755-766.
Duerre, J. A. et al., (1971) *Fed. Proc.* 30, 1067.
Federle, M. J. et al. (2001) *J. Clin. Invest.* 112, 1291-1299.
Grauert, M. et al. (1985) *Liebigs*, Ann. Chem. 1817-1824.
Lewis, H. A. et al. (2001) *Structure* 9, 527-537.
Lorand, J. P. et al. (1959) *J. Org. Chem.* 24, 769-774.
Meijler, M. M. et al. (2004) *Angew. Clem. Int. Ed. Engl.* 43, 2106-2108.
Michel, P. et al. (2003) *Synthesis* 10, 1 598-1602.
Miller, S. T. et al. (2004) *Mol. Cell.* 15, 677-687.
Schauder, S et al. (2001) *Mol. Microbiol.* 41, 463-476.
Schmid, C. R. et al. (1992) *Synthesis*, 587-590.
Semmelhack, M. F. et al. (2004) *Org. Lett.* 6, 2635-2637.
Slaughter, J. C. (1999) *Biol. Rev.* 74, 259-276.
Springsteen, G. et al. (2002) *Tetrahedron* 58, 5291-5300.
Surette, M. G. et al. (1999) *Proc. Natl. Acad. Sci. USA* 96, 1639-1644.
Van Duin, M. et al. (1985) *Tetrahedron Lett.* 41, 3411-3412.
Vekemans et al. (1985) *Recl. Trav. Chim. Pays-Bas.* 104, 266-272.
Winzer, K. et al. (2002) *Microbiology* 148, 909-922;
Xavier, K. B. et al. (2003) *Curr. Opin. Nicrobiol.* 6, 191-197.
Yoshida, J. et al. (1992) *J. Chem. Soc. Perkin* 1, 343-350.
Zibuck, R. et al. (1988*Helv. Chim. Acta* 71, 237-240.
Zhu, J. G. et al. (2003) *J. Am. Chem. Soc.* 125, 13379-13381.

We claim:

1. A method to synthesize protected DPD which comprises
   a) reacting gluconic acid γ-lactone with dimethoxycyclohexanone for a time and under conditions to produce 5,6-O-cyclohexylidene-glucono-1,4-lactone;
   b) subjecting said lactone to oxidative cleavage to produce 2,3-O-cyclohexylidene-glyceraldehyde;
   c) halogenating said glyceraldehyde under conditions to produce 1,1-dihalo-3,4-cyclohexylidenedioxybut-1-ene ("dihaloalkene");
   d) purifying said dihaloalkene and further reacting said dihaloalkene under conditions to convert the alkene moiety of said dihaloalkene to an alkyne anion;
   e) quenching said anion with either
      i) a methylating agent to produce 1,1-dihalo-3,4-cyclohexylidenedioxypent-3-yne, or
      ii) water to produce 1,1-dibromo-3,4-cyclohexylidenedioxybut-3-yne, followed by methylation to produce 1,1-dibromo-3,4-cyclohexylidenedioxypent-3-yne, and recovering said alkyne;
   f) oxidizing said alkyne in non-aqueous solution under conditions to produce 4,5-cyclohexylidenedioxy-2,3-pentadione, which is said protected DPD; and
   g) recovering said protected DPD.

2. The method of claim 1, wherein said gluconic acid γ-lactone is a racemic mixture of the L- and D-stereoisomers of gluconic acid γ-lactone and said protected DPD is a racemic mixture of (S)-4,5-cyclohexylidenedioxy-2,3-pentadione and (R)-4,5-cyclohexylidenedioxy-2,3-pentadione.

3. A method to stereospecifically synthesize protected DPD which comprises
   a) reacting the desired stereoisomer of gluconic acid γ-lactone with dimethoxycyclohexanone for a time and under conditions to produce 5,6-O-cyclohexylidene-glucono-1,4-lactone;
   b) subjecting said lactone to oxidative cleavage to produce 2,3-O-cyclohexylidene-glyceraldehyde;
   c) halogenating said glyceraldehyde under conditions to produce 1,1-dihalo-3,4-cyclohexylidenedioxybut-1-ene ("dihaloalkene");
   d) purifying said dihaloalkene and further reacting said dihaloalkene under conditions to convert the alkene moiety of said dihaloalkene to an alkyne anion;
   e) quenching said anion with either
      i) a methylating agent to produce 1,1-dihalo-3,4-cyclohexylidenedioxypent-3-yne, or
      ii) water to produce 1,1-dibromo-3,4-cyclohexylidenedioxybut-3-yne, followed by methylation to produce 1,1-dibromo-3,4-cyclohexylidenedioxypent-3-yne, and recovering said alkyne;
   f) oxidizing said alkyne in non-aqueous solution under conditions to produce 4,5-cyclohexylidenedioxy-2,3-pentadione, which is said protected DPD; and
   g) recovering said protected DPD having the desired stereospecificity.

4. The method of claim 1, wherein said gluconic acid γ-lactone is L-gluconic acid γ-lactone and said protected DPD is (S)-4,5-cyclohexylidenedioxy-2,3-pentadione.

5. The method of claim 1, wherein said gluconic acid γ-lactone is D-gluconic acid γ-lactone and said protected DPD is (R)-4,5-cyclohexylidenedioxy-2,3-pentadione.

6. The method of claim 1 or 3, wherein isotopically labelled compounds are produced by using a methylating agent with an isotope of carbon-12 in step e).

7. The method of claim 6, wherein the isotope is $^{13}C$ or $^{14}C$.

8. A method to synthesize protected DPD which comprises
a) preparing an 5,6-O-alkylidene-protected gluconic acid γ-lactone having a protecting group represented by the formula wherein R is independently alkyl having from 3 to 8 carbon atoms, aryl, or when taken together, form a cycloalkyl ring having from 4 to 8 carbon atoms;
b) subjecting said lactone to oxidative cleavage to produce 2,3-O-alkyldeneglyceraldehyde;
c) halogenating said glyceraldehyde under conditions to produce a 1,1-dihalo-3,4-alkylidenedioxybut-1-ene ("dihaloalkene");
d) purifying said dihaloalkene and further reacting said dihaloalkene under conditions to convert the alkene moiety of said dihaloalkene to an alkyne anion;
e) quenching said anion with either
   i) a methylating agent to produce 1,1-dihalo-3,4-alkylidenedioxypent-3-yne, or
   ii) water to produce 1,1-dibromo-3,4-alkylidenedioxybut-3-yne, followed by methylation to produce 1,1-dibromo-3,4-alkylidenedioxypent-3-yne, and recovering said alkyne;
f) oxidizing said alkyne in non-aqueous solution under conditions to produce 4,5-alkylidenedioxy-2,3-pentadione, which is said protected DPD; and
g) recovering said protected DPD.

* * * * *